United States Patent [19]

Timm

[11] Patent Number: 5,704,893
[45] Date of Patent: Jan. 6, 1998

[54] VESSEL OCCLUSIVE APPARATUS AND METHOD

[75] Inventor: Gerald W. Timm, Minneapolis, Minn.

[73] Assignee: Dacomed Corportion, Minneapolis, Minn.

[21] Appl. No.: 747,999

[22] Filed: Nov. 12, 1996

Related U.S. Application Data

[63] Continuation of Ser. No. 273,418, Jul. 11, 1994, abandoned.

[51] Int. Cl.$^6$ .......................................................... A61F 2/00
[52] U.S. Cl. ...................................... 600/29; 128/DIG. 25
[58] Field of Search ................................... 600/29–32, 38, 600/41; 128/DIG. 25, 686; 606/151–157, 158, 201–203

[56] References Cited

U.S. PATENT DOCUMENTS

| | | |
|---|---|---|
| 3,744,063 | 7/1973 | McWhorter . |
| 3,810,259 | 5/1974 | Summers . |
| 3,863,622 | 2/1975 | Buuck . |
| 4,118,805 | 10/1978 | Reimels . |
| 4,474,187 | 10/1984 | Timm et al. . |
| 4,515,166 | 5/1985 | Timm . |
| 4,571,749 | 2/1986 | Fischell . |
| 4,606,353 | 8/1986 | Timm . |
| 4,731,083 | 3/1988 | Fischell . |
| 4,766,909 | 8/1988 | Timm et al. . |
| 4,784,660 | 11/1988 | Fischell . |
| 4,829,990 | 5/1989 | Thuroff et al. . |
| 4,848,361 | 7/1989 | Penney et al. . |
| 4,911,176 | 3/1990 | Timm et al. . |
| 4,958,630 | 9/1990 | Rosenbluth et al. . |
| 5,184,629 | 2/1993 | Erickson et al. . |

FOREIGN PATENT DOCUMENTS

WO 84/01098  3/1984  WIPO .

OTHER PUBLICATIONS

Exhibit A: Product Information Brochure, *Snap–Gauge®* *Impotence Screening Device*, by Dacomed Corporation, 1 pg. (1988) (Form No. 710–036–1089).

Exhibit B: Brochure, *Don't Think of it as Simply an Addition to Your Practice, Think of it as Multiplication*, by Dacomed Corporation, 1 pg. (1989).

Exhibit C: Product Information Brochure, *Rigiscan Ambulatory Rigidity & Tumescence Monitor*, by Dacomed Corporation, 1 pg. (1989) (Form No. 750–197–0389).

Exhibit D: Product Information Brochure, *Rigiscan® DT Monitor*, By Dacomed Corporation, 1 pg. (1988) (Form No. 750–261–1089).

Exhibit E: Brochure, *Finally, A Way To Control Male Incontinence Without All The Risk*, by Dacomed Corporation, 1 pg. (1989).

Exhibit F: Product Information Brochure, $C^3$™ *Male Continence Device*, by Dacomed Corporation, 1 pg. (1989) (Form No. 910–279–0194).

Abstract of Societe Internationale D'Urologie, 23rd Congress, Sep. 18–22, 1994, Sydney, Australia.

Abstract of American Urological Association, "IC#13 Artificial Urinary Sphincters," May 15, 1994, San Francisco, California.

*Urologic Clinics of North America*, vol. 16, No. 1, Feb., 1989, pp. 99–117.

*IEEE Transactions on Bio–Medical Engineering*, vol. BME–17, No. 4, Oct., 1970, pp. 352.

*J. Biomechanics*, vol. 4, pp. 213–219, 1971.

*Primary Examiner*—John P. Lacyk
*Attorney, Agent, or Firm*—Merchant, Gould, Smith, Edell, Welter & Schmidt, P.A.

[57] ABSTRACT

The present invention relates to a vessel occlusive apparatus for reversibly occluding a fluid conveying vessel in a human and/or animal. In one embodiment the vessel occlusive apparatus comprises an elongated member at least partially encircling the vessel, and means connected to the elongated member for applying tension to the elongated whereby pressure is applied to the vessel to prevent fluid from passing therethrough.

23 Claims, 5 Drawing Sheets

VESSEL OCCLUSIVE APPARATUS AND METHOD

This is a continuation of application Ser. No. 08/273,418, filed Jul. 11, 1994 now abandoned.

BACKGROUND OF THE INVENTION

The present invention relates to an apparatus and method for occluding fluid conveying vessels in the body. In particular, the invention relates to an apparatus and method for occluding the urethra so as to restore urinary continence to patients with urinary control problems.

Urinary incontinence is a frequent and distressing sequel to various neurological diseases, surgical procedures, spinal cord injury, etc. Various urethral occlusive apparatus have been developed in an effort to restore urinary continence to patients with urinary control problems.

In particular, apparatus utilizing hydraulic sphincters or cuffs have been used to provide urethral occlusion. See for example:

Timm, G. W., Merrill, D. E. and Bradley, W. E. "Intermittent Occlusion System", IEEE Transactions On Bio-Medical Engineering, BME-17:352, 1970.

Timm, G. W., "An Implantable Incontinence Device", J. Biomechanics, 4:213–219, 1971.

U.S. Pat. No. 3,744,063; issued Jul. 10, 1973.

U.S. Pat. No. 3,863,622; issued Feb. 4, 1975.

U.S. Pat. No. 4,571,749; issued Feb. 25, 1986.

U.S. Pat. No. 4,731,083; issued Mar. 15, 1988.

U.S. Pat. No. 4,784,660; issued Nov. 15, 1988.

One particular problem with hydraulic sphincters or cuffs is that they often do not apply uniform pressure on the urethra. As the cuff or sphincter is inflated it folds or changes its shape, often in a non-uniform manner, thereby exerting uneven occlusion force on the urethra. This can result in urethral erosion or urethra tissue being worn away after extensive use.

Another approach to treating urinary incontinence is to surgically adjust the angle between the urethra and the bladder. This angle is often referred to as the angle of the urethro vesical junction. Of course a problem with this procedure is that the effects of the surgery cannot be readily changed and requires trained medical professionals to do so.

The present invention offers a substantial improvement over existing urethral occlusive apparatus and methods.

SUMMARY OF THE INVENTION

The present invention relates to an occlusive apparatus and method for reversibly occluding fluid conveying vessels in the body.

The present invention has numerous applications for controlling and/or occluding fluid flow in fluid conveying vessels in humans and/or animals. Its applications include control of fecal incontinence, venous outflow from a penus and thus impotence, bile duct flow, male and female fertility, blood flow in blood vessels, etc. The present invention can be used in conjunction with most any vessel in the body. In many applications the present invention will occlude the vessel as required to stop or prohibit fluid flow. In other applications the present invention will control the amount of fluid flow through the vessel.

One embodiment of the present invention relates to an occlusive apparatus and method for reversibly occluding the urethra of a patient.

In a preferred embodiment, the urethral occlusive apparatus and method includes an elongated member at least partially encircling the urethra. Means is connected to said elongated member for placing the elongated member under tension, whereby occlusive force is applied to the urethra to prevent fluid from passing through.

In one embodiment, the elongated member substantial surrounds the circumferential extent of the urethra so as to form an annulus about the urethra. When the elongated member is placed under tension, the diameter of the annulus is reduced thereby exerting a radially inward directed force which occludes the urethra.

In yet another embodiment, the elongated member only partially surrounds the circumference of the urethra. When the elongated member is placed under tension, the elongated member exerts, at least in part a lateral bending force on the urethra so as to change the angle of the urethra thereby occluding the urethra.

In one embodiment of the present invention the elongated member is partially enclosed in a flexible sheath. The sheath shields the elongated member from the urethra. Preferably the sheath is made from a material which has little or no folding occur as the elongated member is tensioned.

In a preferred embodiment of the invention the sheath is made of expanded polytetrofloraethylene (expanded PTFE).

In one embodiment, the elongated member is partially, slidably disposed in a substantially non-compressible tube. The sheath is suitably attached proximate at least one end of the sheath to the tube. If the elongated member forms an annulus about the urethra, the sheath is suitable connected at both ends of the sheath to the tube. Accordingly as the elongated member is tensioned or pulled, the length of the sheath contracts thereby exerting force on the urethra.

In one embodiment a pulley and spring assembly is used to tension the elongated member. In still one embodiment, the pulley assembly is manually activated, and in yet another embodiment the pulley is motor driven.

In one embodiment the pulley assembly includes two pulleys mounted for pivotal movement about a common axis. The two pulleys are interconnected by a coiled spring which serves as a shock absorber to take up any slack in the system and to absorb excessive force or resistance encountered during operation thereby resulting in smoother operation of the apparatus. The spring additionally keeps the elongated member in tension which thereby creates a preset occlusive force around the urethra.

In yet another embodiment, the present invention pertains to an electro-mechanical apparatus and method for exerting an urethral occlusive force which utilizes an abdominal pressure sensor providing input signals representative of the extravesical, abdominal pressure to an electronic controller which controls the tension of the elongated member in response to the input signals received from the pressure sensor.

A preferred embodiment of the present invention is totally implantable in the body of the patient.

In yet another embodiment, the implantable apparatus requires no tubes, wires, or other external control mechanisms passing through the skin of the patient.

An advantage of one embodiment of the present invention is that it does not use a hydraulic cuff or sphincter mechanism. As a result it is able to apply a more uniform radial force against the circumference of the urethra when occluding the urethra.

These and various other features and advantages of novelty which characterize the invention are pointed out with particularity in the claims annexed hereto and forming a part hereof. However, for a better understanding of the invention, its advantages and objects obtained by its use, reference should be had to the drawings which form a further part hereof, and to the accompanying descriptive matter, in which there is illustrated and described a preferred embodiment of the invention.

BRIEF DESCRIPTION OF THE DRAWINGS

In the drawings in which like reference numerals and letters generally indicate corresponding parts throughout the several views.

DETAILED DESCRIPTION OF PREFERRED EMBODMENT(S)

As noted above, the apparatus and method of the present invention might be utilized in conjunction with any number of different vessels in humans and animals which are used to convey fluid. The following are some examples of various applications of the present invention; however, this list is by no means exhaustive of the numerous applications in which the present invention may be used. The present invention might be used to control fecal incontinence or bowl movements, to control venous outflow from a penis and thus impotence, to control bile duct flow, to control fluid flow in the vas deferens and thus male fertility, to control fluid flow in the fallopian tubes and thus control female fertility, to control blood flow in blood vessels for vascular studies or the like, etc.

The above noted applications are but a few of the many applications of the present invention. The presention invention will now be described more particularly in view of its application for occluding the urethra and thus controlling incontinence. It will be appreciated that the urethra is shown with only a single lumen or passageway. However, in many applications such as controlling venous outflow from the penis, there are multiple lumens which will be occluded by the present invention.

A urethral occlusive apparatus method in accordance with the present invention in the preferred embodiment is designed to be totally implantable. The apparatus has no tubes or wires or other electro-mechanical connection passing through the skin. Additionally, in the preferred embodiment no external appliances are required to operate the system. However, coupled coils might be used either for continuous powering of the device or to recharge batteries which are implanted to power the device. Preferably, the complete device is capable of being inserted using existing endoscopic or other minimally invasive techniques.

In the preferred embodiment, the urethral occlusive apparatus is made of materials and has a geometric configuration which is compatible with the body. In one embodiment, materials used might include titanium, stainless steel or implantable grade plastics, and the apparatus might have a dimension of 1×3×5 cm. In the preferred embodiment, all surfaces in contact with body fluids and/or tissue meet the required; e.g., class 6 U.S.P., tests for toxicity and pyrogenicity. In addition, the corners and edges are rounded and surfaces are nonabrasive to body structures. The urethral apparatus of the preferred embodiment is also lightweight so as to minimize any chance for migration. One embodiment might weigh 100 grams.

In the preferred embodiment, the operation of the urethral apparatus is easily understood and readily controlled by the user requiring a minimal amount of manual or mental dexterity. Activation and/or deactivation shall be accomplished through the intact skin. The activation/deactivation mechanism of the urethral apparatus shall be of a size to be readily grasped by the user. In alternative embodiments the activation/deactivation device may be electro-magnetically controllable or controlled by other wireless means such as coupled coils or radio frequency (RF) signals. In yet other embodiments, a tensioning algorithm shall be modifiable from outside the body.

In the preferred embodiment, the occlusive force exerted against the urethra shall be sufficient to prevent urinary leakage but not so great the urethra viability is impaired. Preferably, the pressure shall not exceed 100 cm H2O for more than 10 minutes when in the activated state. Moreover, the urethral apparatus shall not interfere with urine flow when in the open or deactivated state.

Alternate embodiments of the urethral apparatus shall have automatic pressure release capabilities with high intravesical pressure. In one preferred embodiment, a detrusor muscle contraction (bladder muscle contraction) producing an intravesical pressure greater than 120 cm H2O (estimated normal voiding pressure) shall result in release of pressure against the urethra upon being sensed by an abdominal sensor present in the urethral apparatus.

Preferably, a nonfunctioning urethral apparatus shall leave the patient in his/her preimplant incontinent condition. The device shall be inert in the presence of body tissues, and materials contained within the urethral apparatus shall be of an implantable quality and be nonallergenic to the patient. Preferably the mechanism will prevent leakage during coughing, straining or other sudden increases in abdominal pressure. A preferred embodiment of the system shall contain a sensor to be placed in the abdominal cavity to feed back tensioning information to the controller. The sensor senses intraabdominal, extravesical pressure that causes intravesical pressure (i.e. bladder pressure) to rise without a detrusor muscle contraction. When this occurs in the presence of impaired urinary sphincter contractibility, urinary incontinence occurs. The sensor could also sense neural impulses related to detrusor muscle activity and cause the urethral apparatus to respond appropriately.

Preferably materials used in the system shall not deteriorate in contact with body fluids and tissue or as to provide the urethral apparatus with long-term usage. In the preferred embodiment, the maximum activation pressure obtainable in the system shall be inherent and therefore not dependent upon the ability of the user to manipulate the device.

Figure 1:
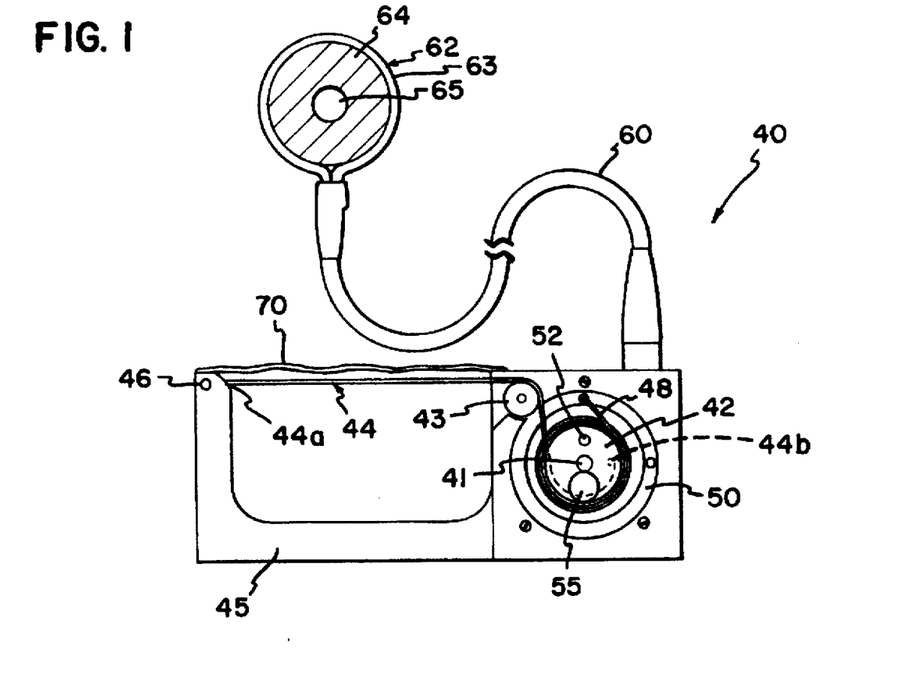
FIG. 1 is a side elevational view in partial cross-section illustrating an embodiment of a urethral occlusive apparatus in accordance with the principles of the present invention.
Figure 2:
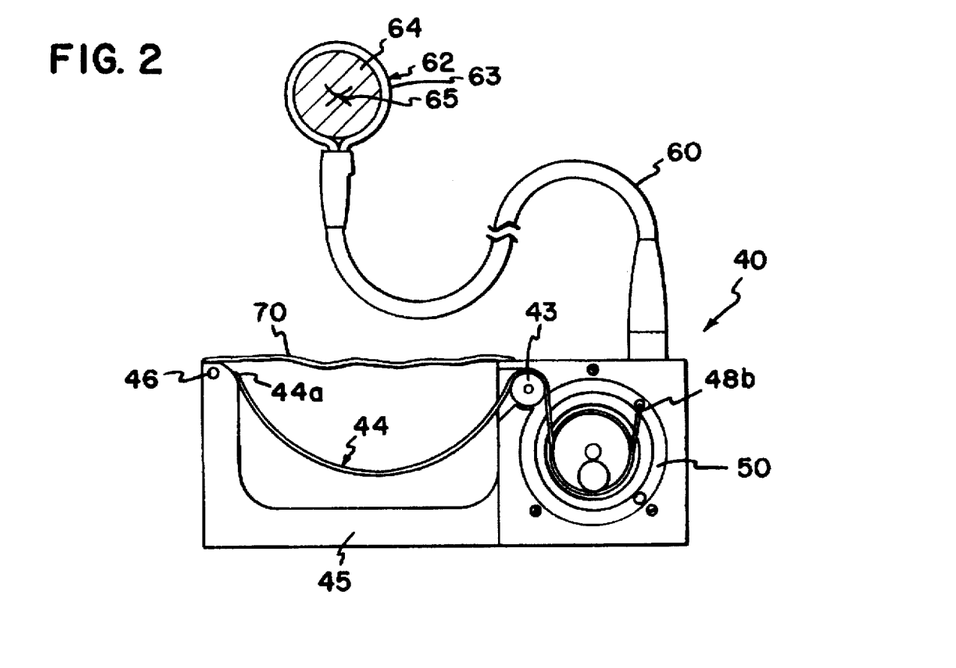
FIG. 2 is a side elevational view of the embodiment shown in FIG. with the occlusive device activated so as to occlude the urethra.
Figure 3:
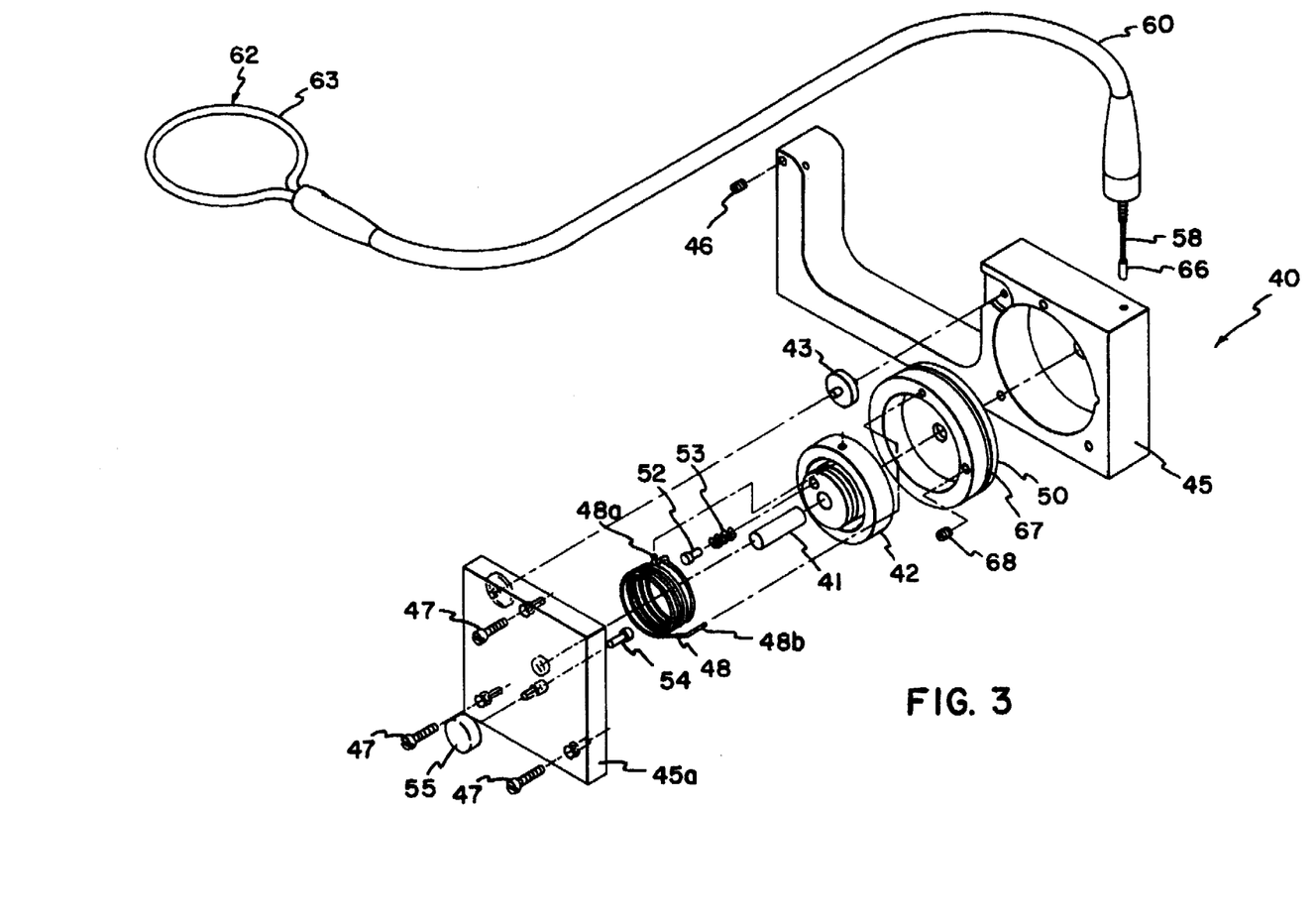
FIG. 3 is an exploded view of the embodiment shown in FIGS. 1 and 2.

More particularly, there is illustrated in FIGS. 1-3, a preferred embodiment of the present invention, generally referred to by the referenced numeral 40. The urethral apparatus 40 includes a pulley 42 mounted for pivotal movement about an axial member 41 defining an axis of rotation. A member 44 extends over a guide pulley 43 and around the pulley 42. The member 44 is connected proximate a first end 44a to a housing 45 of the urethral apparatus 40 by a fastener 46. An opposite end 44b of the member 44 is suitably fastened to the pulley 42 in a groove formed in the pulley 42. In one embodiment the member 44 might be directly attached or attached after only a partial revolution to the pulley 42 and in still in another embodiment the member 44 might be wrapped around the pulley 42 one or more complete revolutions.

A coiled spring 48 is coaxially mounted about the pulley 42. A first end 48a of the coiled spring 48 is suitably fastened to the pulley 42 and a second end 48b is suitably fastened to a large diameter pulley 50 which is pivotable about the axis 41. A pin 52 biased axially by a coil spring 53 is alignable with a pin 54 upon rotation of the pulley 42 a predetermined distance in a clockwise direction. The pin 54 is slideably mounted in a housing portion 45a and has a push button 55 attached at the end of the pin 54. In the embodiment shown, the housing portion 45a is suitably mounted to the rest of the housing by fasteners 47. When the pin 52 is aligned with the pin 54, the pin 52 axially biases the pin 54 and projects into a bore of the housing 45a where the pin 54 is slideably disposed. The push button 55 can be used to force the pin 54 axially back toward the pin 52 such that the pin 52 is forced out of the bore of the housing 45a, whereby the pulley 42 is caused to rotate counter clockwise due to the tension in the spring 48.

A flexible elongated member such as a cable 58 is disposed in a hollow, axially non-compressible conduit 60 so as to be slidable therein. The cable 58 is preferably substantially non-elastic along its longitudinal axis so that exerting a force and causing movement of a first proximal end of the cable 58 will cause a corresponding movement of the cable 58 at a second distal end. A distal end portion of the cable 58 extends from an open end 61 of the conduit 60 and is looped back and suitably attached to the end of 61 of the conduit 60 so as to form an annulus 62 which can be positioned to surround a urethra 64. The distal end portion of the cable 58 is slidably enclosed within a sheath 63 which is suitably attached at its ends to the end 61 of the conduit 60. The sheath 63 shields the urethra from the cable 58 and forces against the urethra when the cable 58 is tensioned. In a preferred embodiment, the sheath 63 is made of expanded PTFE.

The conduit 60 is attached to and extends from the housing 45 which houses the pulleys 42,50. A proximal end of the cable 58 is suitably attached to the pulley 50. In the embodiment shown, the proximal end of the cable 58 has a cylinder member 66 suitably attached. The cylinder member 66 is suitably attached in a groove 67 of the pulley 50 by a set screw 68.

While the housing 45 is made of a relatively rigid biocompatible material, a top surface of the housing includes a resilient flexible membrane 70 which is inwardly deformable upon the application of a force so as to displace the member 44 as generally illustrated in FIG. 2. It will be appreciated that this force might simply be applied by a user manually pressing against their skin adjacent the flexible membrane 70.

As illustrated in FIG. 2, upon depressing down on the membrane 70 the member 44 is displaced so as to cause rotation of the pulley 42 which in turn causes rotation of the pulley 50 due to the coil spring 48 interconnecting the pulleys 42, 50. Rotation of the pulley 50 causes tensioning of the cable member 58. As shown in FIG. 2, this results in a subsequent reduction in size of the annulus 62 formed by the cable 48 and the sheath 63, thereby exerting an occlusive force on the urethra 64 so as to close the urethral passage 65 and prevent any leakage.

In the embodiment shown, when the flexible membrane 70 is sufficiently depressed, the pulley 42 rotates the spring biased pin 52 into axial alignment with the pin 54 whereupon the spring biased pin 52 is received in an axial bore of the housing portion 45a where the pin 54 is slideably disposed. Accordingly, when this occurs, the pulleys 42,50 are locked in the activated state thereby maintaining tension on the cable 58 and occluding the urethra 64. To release the tension on the cable 58, the push button 55 is simply pressed from the side of the housing 54 such that the pin 54 forces the pin 52 out of the bore of the housing portion 45a whereupon the pulley 42 is allowed to freely rotate thereby releasing or reducing the tension exerted on the cable 58. Accordingly, the annulus 62 is enlarged and the urethra 64 is no longer occluded.

Figure 4:
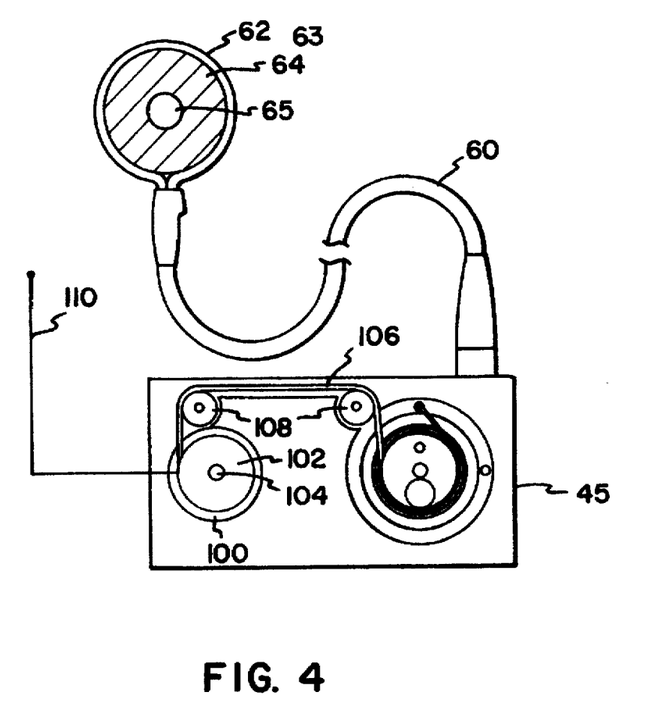
FIG 4 is a diagrammatic view of an alternative embodiment of the present invention including a drive motor.

FIG. 4 is an alternative embodiment of the present invention wherein a motor 100 is provided. The motor 100 includes a pulley 102 mounted on a drive shaft 104 of the motor 100. The pulley 102 is suitably connected to the pulley 42 for rotating the pulley 42. In the embodiment shown, the pulley 102 is connected by an elongated member 106 which is suitably fastened to the drive pulley 102 and the pulley 42. Guide pulleys 108 are shown guiding the elongated member 106. It will be appreciated that the drive motor 100 is powered by a suitable power source interconnected by to the drive motor 100 by an electrical conduit 110. Varying tensions might be placed on the cable member 58 by using the motor 100. Moreover, the motor 100 will preferably include a brake mechanism for retaining the apparatus in an activated state. The drive motor might be activated manually or automatically activated according to certain predetermined conditions.

Figure 5A:
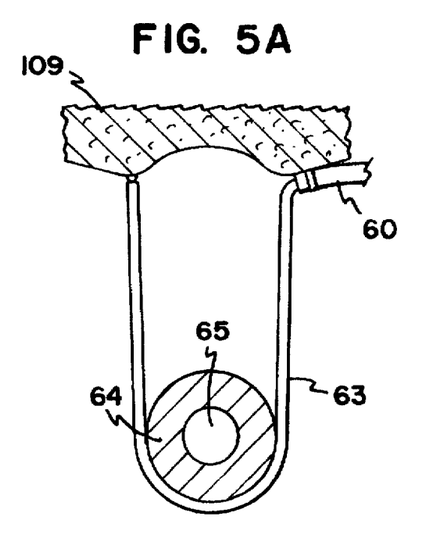
FIGS. 5A, B are diagrammatic views of still another embodiment of a urethral occlusive apparatus which has a distal end of an elongated member anchored to bone on one side of the urethra, the elongated member being slidable in an outer sleeve member which is attached to bone on the other side of the urethra.
Figure 5B:
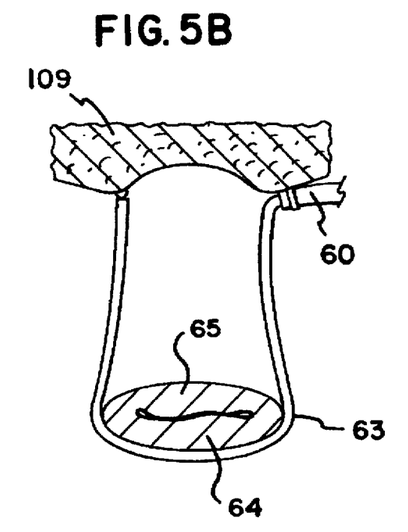
Figure 6A:
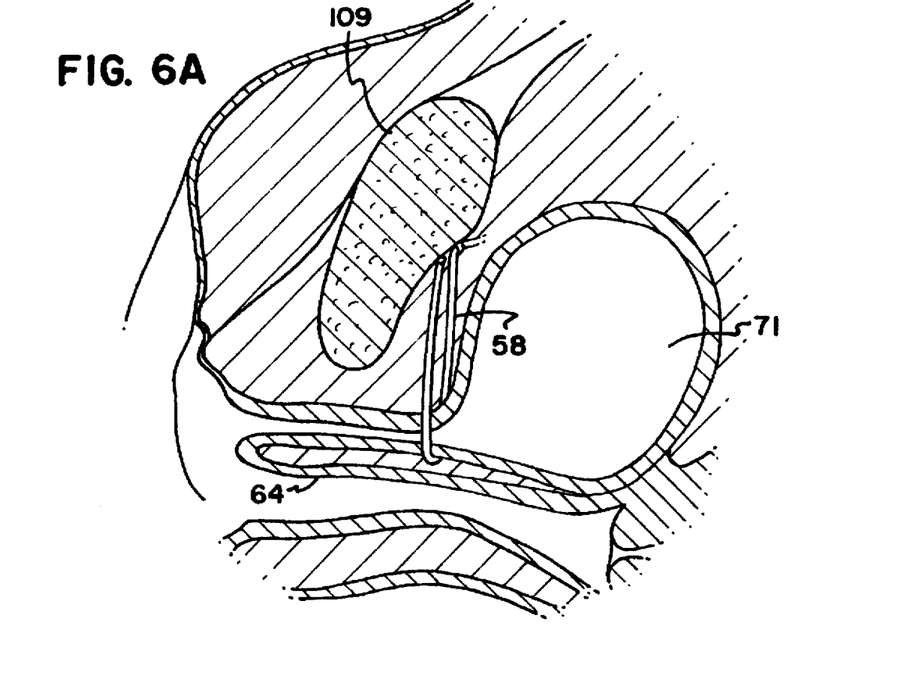
FIGS. 6A, B are diagrammatic views showing the embodiment of FIGS. 5A, B interacting with the urethra.
Figure 6B:
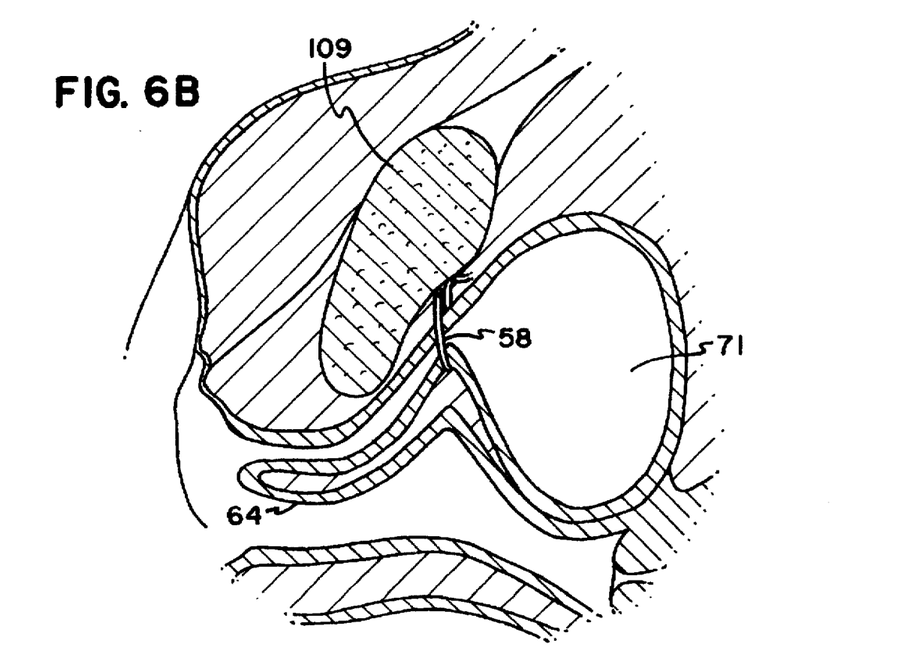

Shown in FIGS. 5A, B is yet another embodiment of the present invention wherein the cable member 58 and sheath 63 are attached proximate a distal end to a pubic bone structure 109 in the body on one side of the urethra 64. The sheath 63 is connected to the conduit 60 proximate a proximal end. The conduit 60 is in turn attached to the pubic bone structure 109 on the other side of the urethra 64. Accordingly, in this embodiment it is not necessary to form an annulus about the urethra. By tensioning or pulling on the cable member 58, the cable member 58 and the sheath 63 cooperate with the bone structure 109 to occlude the urethra 64. The cable 58 and sheath 63 combination exerts in part a lateral bending force on the urethra which bends or kinks the urethra thereby causing occlusion to occur. This is best shown in FIGS. 6A, B where the urethra 64 and bladder 71 are illustrated. In FIG. 6A the urethral device is shown in a relaxed or deactivated state, and in FIG. 6B, the urethral device is shown in an activated or occlusive state.

Figure 7:
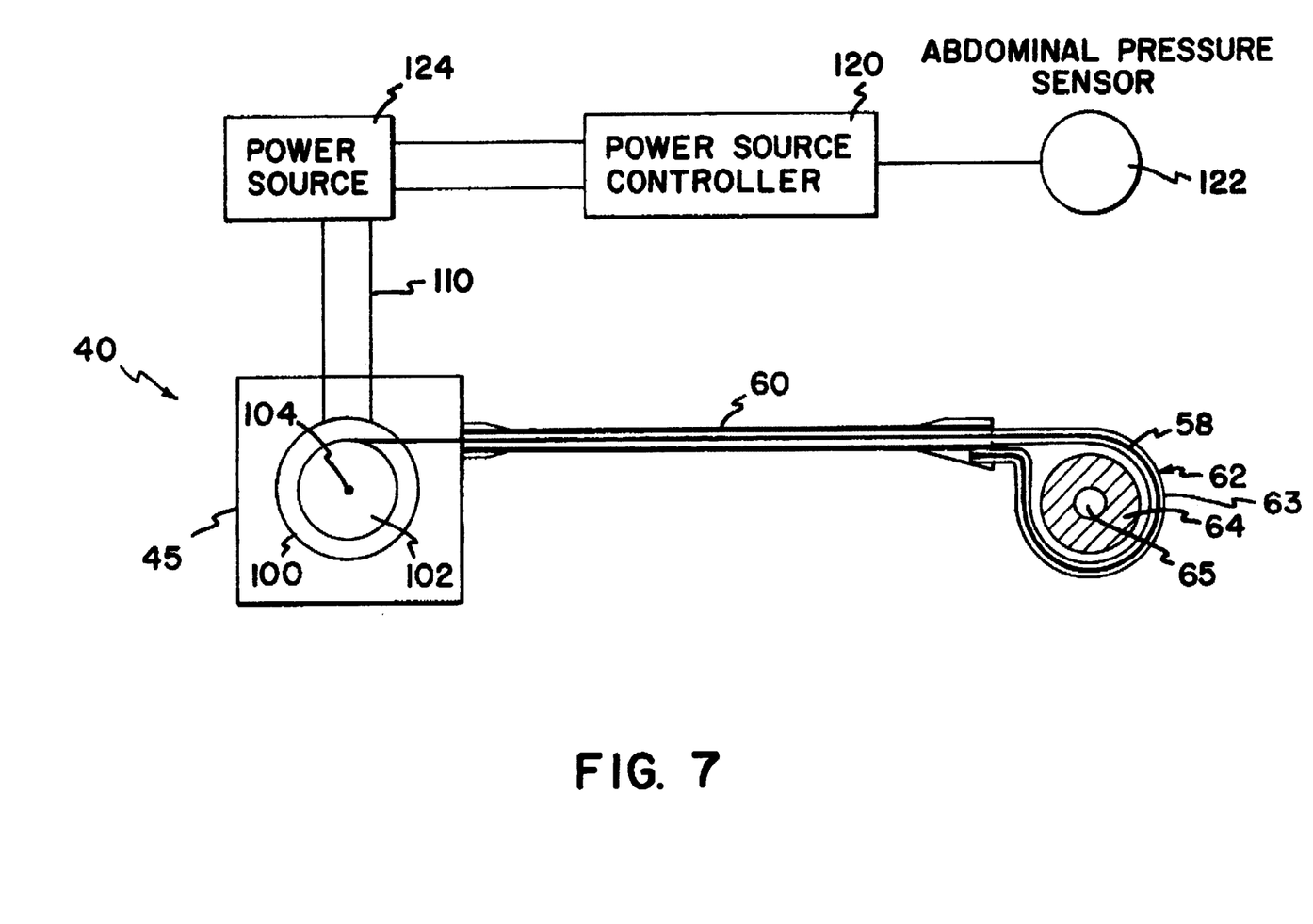
FIG. 7 is a diagraatic view of still another embodiment of a urethral occlusive apparatus including a controller and pressure sensor for automated operation.

Shown in FIG. 7 is yet another embodiment of the present invention which includes a controller 120 electrically connected to an abdominal pressure sensor 122 and a power source 124. The controller 120 is implanted in the body and suitably connected to the motor 100 of the urethral apparatus 40 by the connection 110 for providing current to the motor 100. The pressure sensor 122 is placed in the prevesical space next to the urinary bladder to sense intraabdominal pressure and send signals representative of the pressure so sensed. Upon detection of a predetermined pressure by the pressure sensor 122, the urethral apparatus 40 is activated by the controller 120 according to a predetermined algorithm or preprogrammed logic. The algorithm provides for the tension in the cable to be relaxed when intraabdominal pressure is less than resting bladder pressure of approximately 20 cm H2O. When intraabdominal pressure exceeds 20 cm H2O, tension is applied proportionately until the maximum occlusive pressure at 100 cm H2O is obtained. Cable tension is again released as the intraabdominal pressure drops. Accordingly, the cable is in a relaxed state most of the time, thereby further reducing the risk of urethral erosion.

The power source 124 might include batteries or externally supplied power. The controller 120 might include interface capability for interconnection to various peripherals including an adapter/charger which might be plugged into an AC outlet by a suitable power cord. The interconnection might be accomplished by coupled transformer coils or other suitable methods. This interconnection might also provide for external resetting and/or modification of the predetermined algorithm. Use of interconnection methods such as coupled transformer coils will allow the interface to be accomplished preferably without the use of wires or other physical connectors extending through the skin. It will be appreciated that this embodiment will preferably include program logic which can be readily programmed for different parameter settings, functions, etc. both before implantation of the urethral apparatus 40 or after implantation.

Having read the foregoing description, it is to be understood, that even though numerous characteristics and advantages of various embodiments in accordance with the principles of the invention have been set forth in the foregoing description, together with details of the structure and function of the invention, the disclosure is illustrative only, and changes may be made in detail, especially matters of shape, size and arrangement of the parts within the principles of the invention to the full extent indicated by the broad general meaning of the term in which the appended claims are expressed.

What is claimed is:

1. An occlusive apparatus for reversibly occluding a fluid conveying vessel in a body, comprising:
   an elongated member having a proximal portion and a distal portion, the distal portion of the elongated member being adapted for at least partially encircling the vessel; and
   a tensioning mechanism including a spring structure operatively connected to the proximal portion of said elongated member, the tensioning mechanism being arranged and configured for applying a tensioning force to the proximal portion of the elongated member, wherein when the tensioning force is applied to the proximal portion of the elongated member while the distal portion of the elongated member is at least partially encircling the vessel, the distal portion of the elongated member is caused to apply an occluding pressure to the vessel.

2. An apparatus comprising:
   an elongated member adapted for at least partially encircling an urethra;
   a tensioning mechanism for selectively applying tension to the elongated member;
   abdominal pressure sensor adapted for sensing abdominal pressure; and
   electro-mechanical tension controller interfacing with the abdominal pressure sensor and the tensioning mechanism, the tension controller being arranged and configured for controlling the tension applied to the elongated member by the tensioning mechanism in response to the abdominal pressure sensed by the abdominal pressure sensor.

3. The occlusive apparatus of claim 1, wherein the distal portion of the elongated member is adapted for encircling an urethra, wherein the urethral occlusive apparatus further includes a sensor for determining intra-abdominal pressure and wherein said tensioning mechanism adjusts the tension on the elongated member in response to changing intra-abdominal pressure.

4. The occlusive apparatus of claim 2, wherein said tensioning mechanism is adapted for adjusting the tension applied to the elongated member to release pressure on the urethra if the intravesical pressure exceeds 120 cm of water.

5. The occlusive apparatus of claim 1, wherein said distal portion of said elongated member forms an annulus for encircling the vessel.

6. The occlusive apparatus of claim 1, wherein said distal portion of said elongated member is enclosed in a sheath, whereby said sheath is adapted to press against the vessel as the elongated member is tensioned.

7. The occlusive apparatus of claim 1, wherein the spring structure comprises a constant force spring.

8. The occlusive apparatus of claim 1, wherein the spring structure comprises a torsion spring.

9. The occlusive apparatus of claim 1, wherein the proximal portion of the elongated member slidably extends through a non-compressible conduit and the distal portion of the elongated member extends beyond the conduit.

10. The occlusive apparatus of claim 1, wherein said tensioning mechanism includes means to activate and deactivate said tensioning mechanism, said means to activate and deactivate being operable to activate and deactivate the tensioning mechanism from outside a body.

11. The occlusive apparatus of claim 1, further including a biocompatible, sheath slidably enclosing the distal portion of the elongated member.

12. A method for controlling fluid flow in a fluid conveying body vessel, comprising the steps of:
   encircling at least a portion of the vessel with a distal portion of an elongated member; and
   applying a controlled tensioning force to a proximal portion of the elongated member such that the distal portion of the elongated member is caused to exert a controlled occluding pressure on the vessel to occlude the vessel.

13. A method in accordance with claim 12, wherein the step of encircling includes encircling an urethra for controlling fecal incontinence.

14. A method in accordance with claim 12, wherein the step of encircling includes encircling veins of a penis for controlling venous outflow from the penis.

15. A method in accordance with claim 12, wherein the step of encircling includes encircling a bile duct for controlling bile duct fluid flow.

16. A method in accordance with claim 12, wherein the step of encircling includes encircling vas deferens for controlling fluid flow in the vas deferens thereby providing male fertility control.

17. A method in accordance with claim 12, wherein the step of encircling includes encircling a fallopian tube for controlling fluid flow in the fallopian tube thereby providing female fertility control.

18. A method in accordance with claim 12, wherein the step of encircling includes encircling a blood vessel for controlling fluid flow in the blood vessel.

19. A method for controlling incontinence, comprising the steps of:
    encircling at least a portion of the an urethra with a distal portion of an elongated member;
    applying a tensioning force to a proximal portion of the elongated member so as to occlude the urethra; and
    sensing the intra-abdominal pressure and adjusting the tension of the elongated member based on the pressure sensed.

20. An occlusive apparatus for reversibly occluding a fluid conveying vessel in a body, comprising:
    an elongated member having a proximal portion and a distal portion, the distal portion of the elongated member being arranged to form a loop structure adapted for at least partially encircling the vessel; and
    a tensioning mechanism constructed and arranged to apply a controlled tensioning force to the proximal portion of the elongated member, such that the distal portion of the elongated member is adapted for applying a predetermined occluding pressure to the vessel, wherein the loop structure formed by the distal portion of the elongated member automatically expands or contracts to maintain the predetermined occluding pressure.

21. The occlusive apparatus of claim 20, wherein the tensioning mechanism includes a spring structure operatively coupled to the proximal portion of the elongated member.

22. The occlusive apparatus of claim 21, wherein the spring structure comprises a constant force spring.

23. The occlusive apparatus of claim 21, wherein the spring structure comprises a torsion spring.

* * * * *